United States Patent [19]

Dorsey, III

[11] Patent Number: 5,573,504
[45] Date of Patent: Nov. 12, 1996

[54] COMPOSITE IRRIGATION AND SUCTION PROBE AND VALVE

[75] Inventor: James H. Dorsey, III, Delray Beach, Fla.

[73] Assignee: C. R. Bard, Inc., Murray Hill, N.J.

[21] Appl. No.: 52,080

[22] Filed: Apr. 22, 1993

Related U.S. Application Data

[63] Continuation-in-part of Ser. No. 844,551, Mar. 2, 1992, abandoned, which is a continuation-in-part of Ser. No. 470,771, Jan. 26, 1990, Pat. No. 5,188,591.

[51] Int. Cl.$^6$ ........................................... A61M 1/00
[52] U.S. Cl. ............................ 604/35; 604/33; 604/43; 604/264
[58] Field of Search ..................... 604/35, 37, 39–45, 604/118, 173, 246, 249, 264, 268, 902; 128/4 A; 601/160; 285/921, 321

[56] References Cited

U.S. PATENT DOCUMENTS

| | | | |
|---|---|---|---|
| 1,178,898 | 4/1916 | Young | 604/42 |
| 2,148,541 | 2/1939 | Dierker | 604/40 |
| 3,810,471 | 5/1974 | Truhan | 604/45 |
| 3,921,297 | 11/1975 | Vit | 285/321 |
| 4,149,315 | 4/1979 | Page, Jr. et al. | 604/249 |
| 4,248,589 | 2/1981 | Lewis | 604/45 |
| 4,617,013 | 10/1986 | Betz | 604/39 |
| 4,666,426 | 5/1987 | Aigner | 604/43 |
| 4,878,900 | 11/1989 | Sundt | 285/921 |
| 5,037,386 | 8/1991 | Marcus et al. | 604/43 |

Primary Examiner—John D. Yasko
Assistant Examiner—Mark Bockelman
Attorney, Agent, or Firm—Darby & Darby, P.C.

[57] ABSTRACT

A composite suction and irrigation probe is provided for performing the functions of irrigation and suction alone or simultaneously with the use of a single trumpet valve. The probe consist of an inner cannula and an outer cannula. In the first embodiment the inner cannula is attached to one probe mount end of the valve body while the outer cannula is attached to a second and opposite probe mount end. The inner cannula is inserted through a common channel of the valve body and the outer cannula. In the second embodiment, the inner cannula is attached to the outer cannula prior to attaching the probe to the valve body. The designated suction and irrigation ports located within the common channel of the valve body are isolated from each other to provide discrete and dedicated ports.

25 Claims, 7 Drawing Sheets

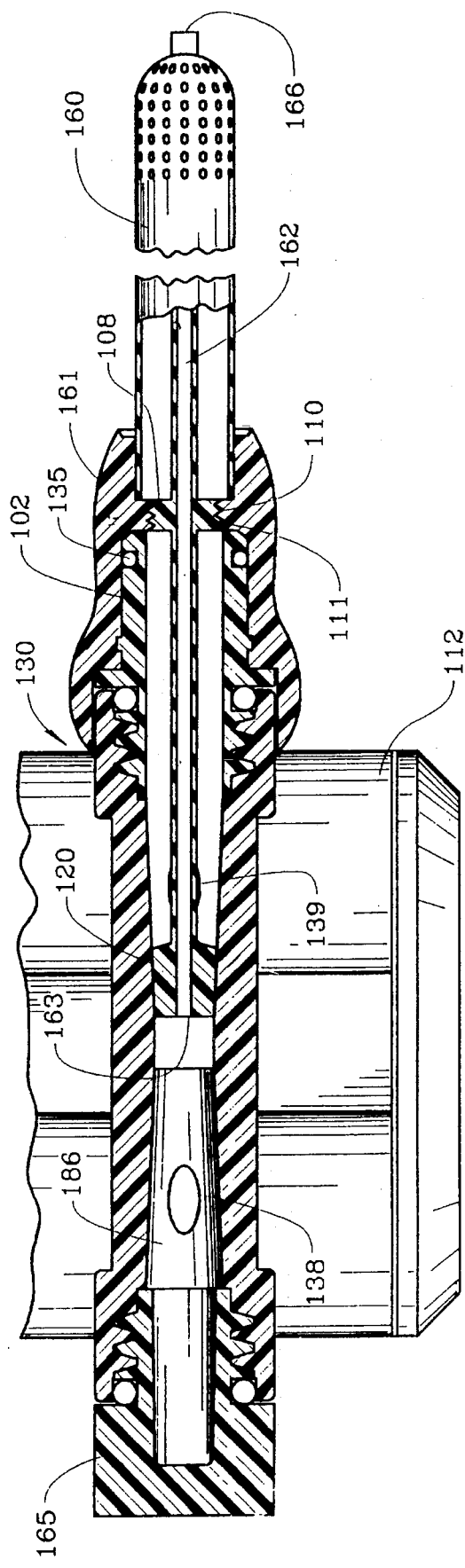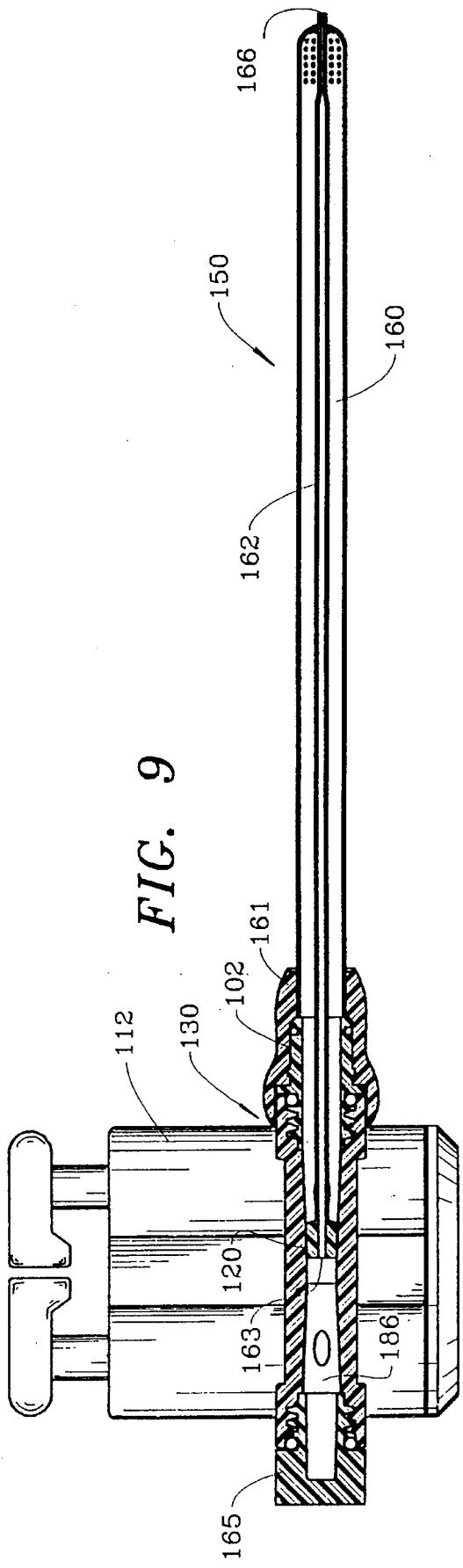

COMPOSITE IRRIGATION AND SUCTION PROBE AND VALVE

This application is a continuation-in-part of U.S. application Ser. No. 07/844,551, now abandoned filed Mar. 2, 1992, which is a continuation-in-part of U.S. application Ser. No. 07/470,771, filed Jan. 26, 1990, now issued as U.S. Pat. No. 5,188,591, on Feb. 23, 1993.

BACKGROUND OF THE INVENTION

1. Field of the Invention

This invention is directed to an apparatus and to a method for use in laproscopic surgery. More specifically, this invention concerns an improved composite suction/irrigation probe for use in conjunction with a hydrodissection apparatus, and to a method involving concurrent infusion and suction of hydrodissection fluid.

2. Description of the Prior Art

Hydrodissection procedures typically involve directing a pressurized fluid stream at a target tissue through a probe, followed thereafter by suction of the fluid from the operative field through the same probe; or, through a probe connected to a separate instrument. This procedure, as practiced with a symmetrical valve (i.e. trumpet valve) of the type disclosed in the U.S. application Ser. No. 07/470,771 filed on Jan. 26, 1990, now issued as U.S. Pat. No. 5,188,591 on Feb. 23, 1993, simply involves the sequential depression of the irrigation piston connected to the source of the hydrodissection fluid, release of the irrigation piston, which discontinues the flow of fluid, depression of the suction piston to effect aspiration of fluid from the operative field, and the repetition of the above sequence. As is thus evident, the sequential infusion of hydrodissection fluid, followed, thereafter, by suction through the same probe prolongs the operative procedures. To the extent that the flow of fluid is interrupted and/or a common channel of the same probe is used for both infusion and aspiration of fluid, the probe tip may become fouled with tissue fragments, blood and the like, thereby interrupting the fluid aspiration process and possibly requiring withdrawal of the probe from the operative field, its replacement and thereafter, the resumption of the operative procedure by reinsertion of the probe into the patient's body.

Without belaboring the foregoing, it is apparent that in order to maintain a clear channel in the hydrodissection (irrigation) probe, it is desirable (if not essential) to (a) maintain a continuous flow of hydrodissection fluid through the probe; and (b) effect aspiration of such fluid from the operative field through a separate probe, or separate channel within a common probe.

In the performance of a hydrodissection procedure of the type described above, it is highly desirable to perform concurrent infusion and aspiration of hydrodissection fluid. This continuous circulation of fluid within the operative field permits rapid clearing of the operative field of debris and, thus, facilitates the operative procedure.

In the event the hydrodissection procedure is performed utilizing a valve (i.e. trumpet valve), concurrent infusion and aspiration of fluid is not readily possible insofar as a common channel, within the valve body, connects each of the valve chambers to one another, and when both plungers are concurrently depressed, the irrigant will begin to flow through the valve body and at the same time a negative pressure is exerted upon the valve body in proximity to the common channel. Accordingly, irrigation fluid will be diverted from flowing into the probe tip by such negative pressure, resulting in it being simply cycled through the valve from the reservoir containing the hydrodissection fluid into the reservoir (fluid trap) associated with suction. The versatility afforded by the design of the trumpet valve has up to now prevented the effective concurrent infusion and aspiration of hydrodissection fluid due to a design limitation inherent in the construction of the valve body. Accordingly, there exists a continuing need to enhance both the versatility of a (trumpet) valve along with its ability to concurrently irrigate and aspirate fluid from an operative field.

SUMMARY OF THE INVENTION

The below and related objects are achieved by providing a symmetrical valve body having at least one pair of valves, one member of said pair connected to a source of pressurized fluid and the other member of said pair connected to a source of negative pressure (vacuum). The symmetry of the valve body allows for connection of a probe tip at either of one or two diametrically opposite positions to accommodate clinician preference (right handed versus left handed operation).

In a first embodiment, a composite probe tip is herein provided to attach to the valve body to each of two mounts on the valve body designed for this purpose. This composite probe includes an outer, or suction, barrel and an inner, or irrigation, barrel, each of which is operatively connected to a different mount on the valve body, however, oriented in a common direction. More specifically, the orientation (mounting) of the suction barrel relative to the valve body is based on clinician preference (right hand versus left hand in operation); and, the irrigation barrel connected to the opposite mount. In mounting of the irrigation barrel to the valve body, it is designed for attachment thereof to the valve body so as to orient it in the same direction as the suction barrel, by passing the irrigation barrel through the valve body and thereby extending down through the suction barrel where it ultimately protrudes from a hole in the tip (distal end) of the suction barrel. This composite probe thus allows for allowing irrigation of the operative field concurrent with the aspiration therefrom.

The irrigation barrel is further provided at its proximal end with a complementary connector for sealing engagement of the valve body at the point where it is connected to the mount. In order to allow for flow of fluid through the irrigation barrel, an opening is positioned on the side of the barrel approximately coincident with an opening in the valve chamber which supplies the pressurized source of irrigation fluid to the barrel, thus affording flow of irrigation through the composite probe to the operative field. Also an embodiment of this inner irrigation tube is a reduced tube that serves to increase velocity of flow rate and increase hydro-dissection abilities.

The infusion of fluid through the inner barrel, and suction of fluid through the outer barrel, requires effective isolation of each member of the composite probe within the valve body. This is achieved by placement of a flexible "O" ring on the irrigation barrel which is positioned near the proximal end thereof to effectively seal the common passageway (channel) which connects each of the valve chambers to one another.

In operation of a hydrodissection valve as described above, a source of suction is connected to the valve body so as to permit the introduction of negative pressure at the tip of the suction barrel upon movement/depression of the piston within a valve chamber operatively connected to the source of negative pressure; and infusion of pressurized fluid to the tip of the irrigation barrel upon movement/depression of the piston within a chamber operatively associated with a source of irrigation fluid. Insofar as each of the source of negative pressure and pressurized fluid are isolated by one another within the valve body by the "O" ring seal on the irrigation barrel, it is possible to depress either one or both pistons concurrently and thereby infuse fluid into the operative field and aspiration thereof within a single symmetrical instrument. Concurrent depression of these pistons will result in concurrent infusion and aspirations of fluid. The continuous flow of fluid through one barrel and aspiration thereof through a different barrel, virtually eliminates the possibility of obstruction of irrigation fluid flow. In the preferred embodiments of this invention, the inner (irrigation) barrel can have a variety of tip configurations. In the most preferred embodiment to this invention, the probe tip is tapered. This increases pressure and flow rate of the fluids. It is also contemplated that the respective functions of each member of the composite probe be reversed simply by reversal of the connection of the pressurized source of irrigation fluid and negative pressure to the valve body.

It is the object of this invention to remedy the above as well as related deficiencies in the prior art.

More specifically, it is the principal object of this invention to provide enhancement in the operation of a symmetrical hydrodissection valve body to allow for concurrent infusion and aspiration of hydrodissection fluid.

It is another object of this invention to provide a composite probe tip adapted for use in conjunction with a symmetrical hydrodissection valve to allow for concurrent irrigation and aspiration of fluid therethrough.

It is yet another object of this invention to provide an improved hydrodissection method involving concurrent infusion and aspiration of hydrodissection fluid.

In accordance with these and other objects which will be apparent hereinafter, the instant invention will now become described with particular reference to the accompanying drawings. The drawings constitute a part of this specification and include exemplary embodiments of the present invention and illustrate various objects and features thereof.

BRIEF DESCRIPTION OF THE DRAWINGS

The invention may be better understood by reference to the drawings in which:

FIG. 9 is a cross sectional view of the symmetrical trumpet valve equipped with the second embodiment composite probe of the present invention;

FIG. 10 is a partial closeup view of FIG. 9 illustrating the second embodiment of the present invention;

DESCRIPTION OF THE PREFERRED EMBODIMENTS

Figure 1:
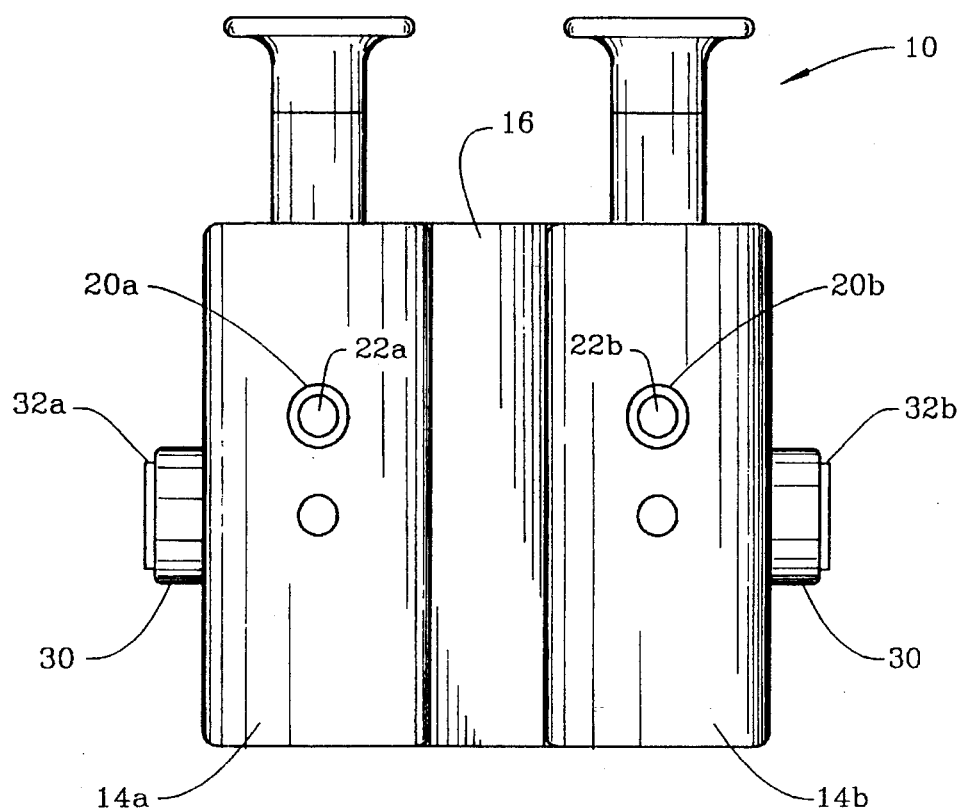
FIG. 1 is a plan view of a symmetrical irrigation control valve of this invention.

The preferred embodiments of this invention are illustrated in reference to the foregoing enumerated Figures. For ease of discussion and simplification of description, a common reference numeral is assigned to a particular component feature of the irrigation control valve and such common reference numeral used within each of the Figures.

In the illustration of this invention shown in FIG. 1, the irrigation valve 10 comprises a valve housing or body 12 having two valve chambers 14a, 14b, one valve chamber adapted for communication between a common conduit 16 of the control valve and a source of irrigation fluid (not shown) and a second valve chamber for communication between a source of suction (not shown) and a common conduit 16 of the control valve body. In each instance, the common conduit of the control valve is provided with a probe (not shown). This probe can be connected to either the right hand or left and fitting located on the side of the control valve. The positioning of the probe relative to the body of the control valve will be based upon clinician preference— whether the clinician is right handed or left handed. In either instance, the control valve will operate essentially the same. It is also important to note that in the embodiment of this illustration herein either chamber 18a, 18b of the control valve can be connected to either a source of vacuum or a source of irrigation fluid in both chambers, and thus, the preferred embodiments of this invention are essentially the same. In each instance, the irrigation control valve of this invention comprises a valve housing or body within which are formed two cylindrical valve chambers. The housing of the control valve is further equipped with a pair of fittings 20a, 20b for each chamber which defines a conduit 22a, 22b. The fitting can be connected to a source of vacuum or a source of irrigation fluid. These conduits 22a, 22b provide communication between the source of vacuum and/or irrigation fluid and the interior of the valve chamber which is formed within the body of the control valve. The valve chamber is essentially uniform in diameter and of a defined length.

Figure 2:
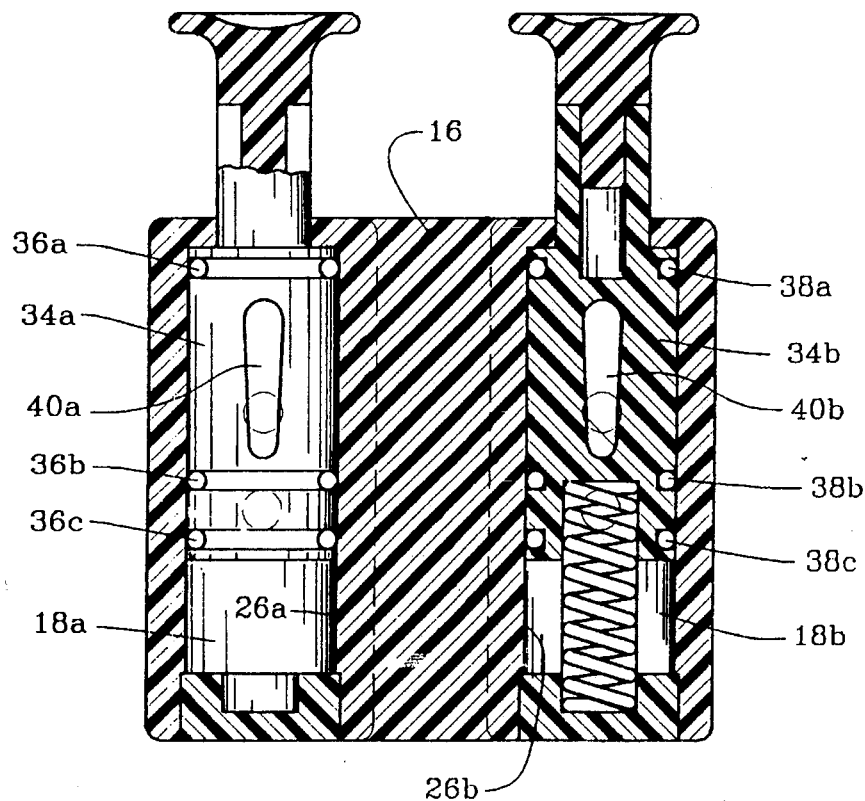
FIG. 2 is a sectional view along the horizontal plane of the irrigation control valve of FIG. 1.
Figure 5:
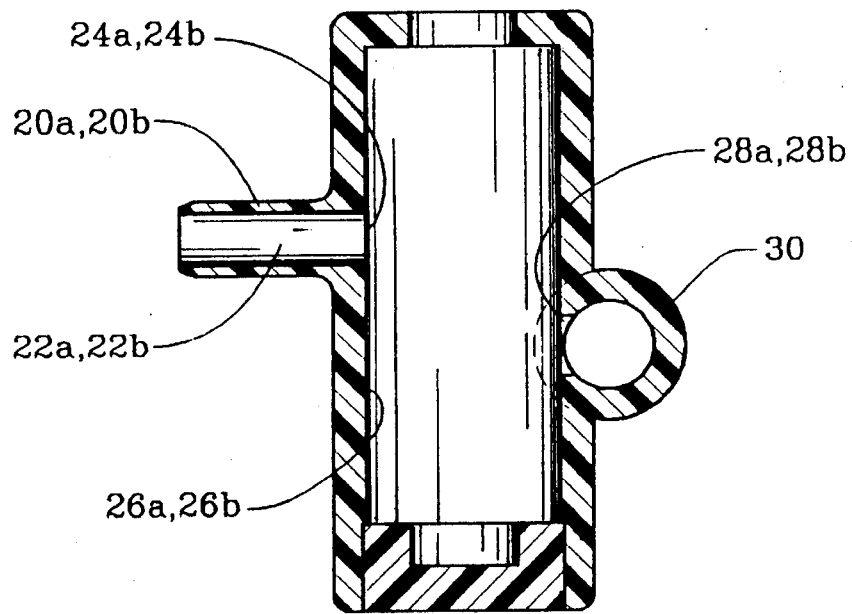
FIG. 5 is a sectional view of the irrigation control valve of FIG. 1.

As more completely illustrated in FIGS. 2 and 5, the valve body defines two interior cylindrical chambers 18a, 18b, each of which is essentially the same in both dimension and in its contemplated operation. Each such chamber is of a defined length. The fitting or inlet port on the valve body defines a conduit which terminates as an inlet orifice 24a, 24b in the chamber wall 26a, 26b. The chamber wall is provided with yet a second orifice 28a, 28b, offset from the inlet orifice. This second orifice provides for communication between the interior of the chamber and a conduit 30 which is at right angles to the orientation of the chamber. This conduit 30 can also be positioned on the same side of the valve body as the inlet orifice 24a, 24b to enhance the ergonomics in the valve design. Of course, the orientation of the piston would be modified accordingly to allow for corresponding modification in the flow path within the valve body. This conduit is provided on either end with a fitting 32a, 32b adapted to connect to a probe (not shown).

Figure 3:
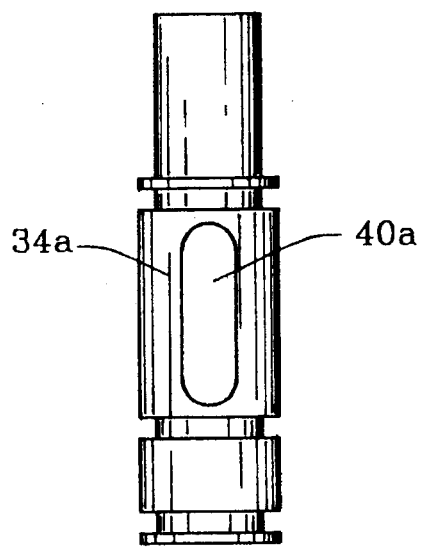
FIG. 3 is a plan view of a piston of the irrigation control valve of FIG. 1.
Figure 4:
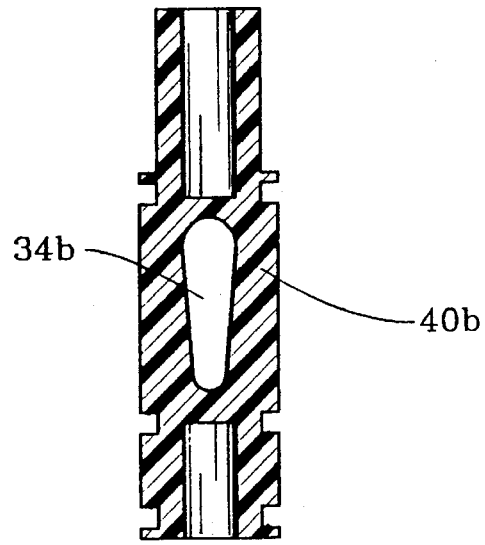
FIG. 4 is a sectional view along the horizontal plane of the piston of FIG. 3.

Each of the valve chambers within the valve body is further provided with a piston 34a, 34b. As more fully illustrated in FIGS. 2, 3, and 4, these pistons are designed for reciprocating movement within the cylinder. In order to provide for watertight and airtight operation, these pistons are each equipped with a series of seals 36a–c, 38a–c. Each piston is further provided with an oval opening 40a, 40b, approximately equivalent in width to the orifices in the chamber wall. The length of the piston is such as to allow reciprocating movement within the cylindrical chamber and accommodation of spring bias means (not shown) within the cylinder chamber between the base of the piston and the bottom of the cylindrical chamber. The spring bias means is intended to maintain the valve in the closed portion.

The seals which are located both fore 36a, 38a and aft 36b, 38b, relative to the oval opening 40a, 40b in the piston prevent fluid from inadvertently flowing from the source of irrigation fluid to the common conduit. As the cylinder is depressed (in the direction indicated by the arrow), and the oval opening in the piston aligned to permit communication between the inlet orifice and the orifice to the common conduit, fluid will begin to flow therebetween. The seal at the base of the piston ensures against fluid being trapped between the base of the piston and the base of the valve chamber which, if not vented, could prevent depression of the piston within the chamber.

FIG. 5 illustrates the relative positioning of the two orifices within each cylinder wall and the contemplated direction of flow of fluid upon reciprocal movement of the piston to allow for such flow.

In operation of this valve, a conduit is connected to each of the fittings on the valve body. The conduit can be connected to either a source of irrigation fluid or to a source of vacuum. For the purpose of simplification of description, it is assumed the conduit is connected to a source of irrigation fluid. Upon depression of the piston, the opening through the piston barrel effects communication between the inlet orifice and the piston wall and the orifice of the common conduit thereby allowing for flow of fluid therebetween. The further the piston is depressed within the valve chamber, the greater the flow of fluid therethrough.

Figure 6:
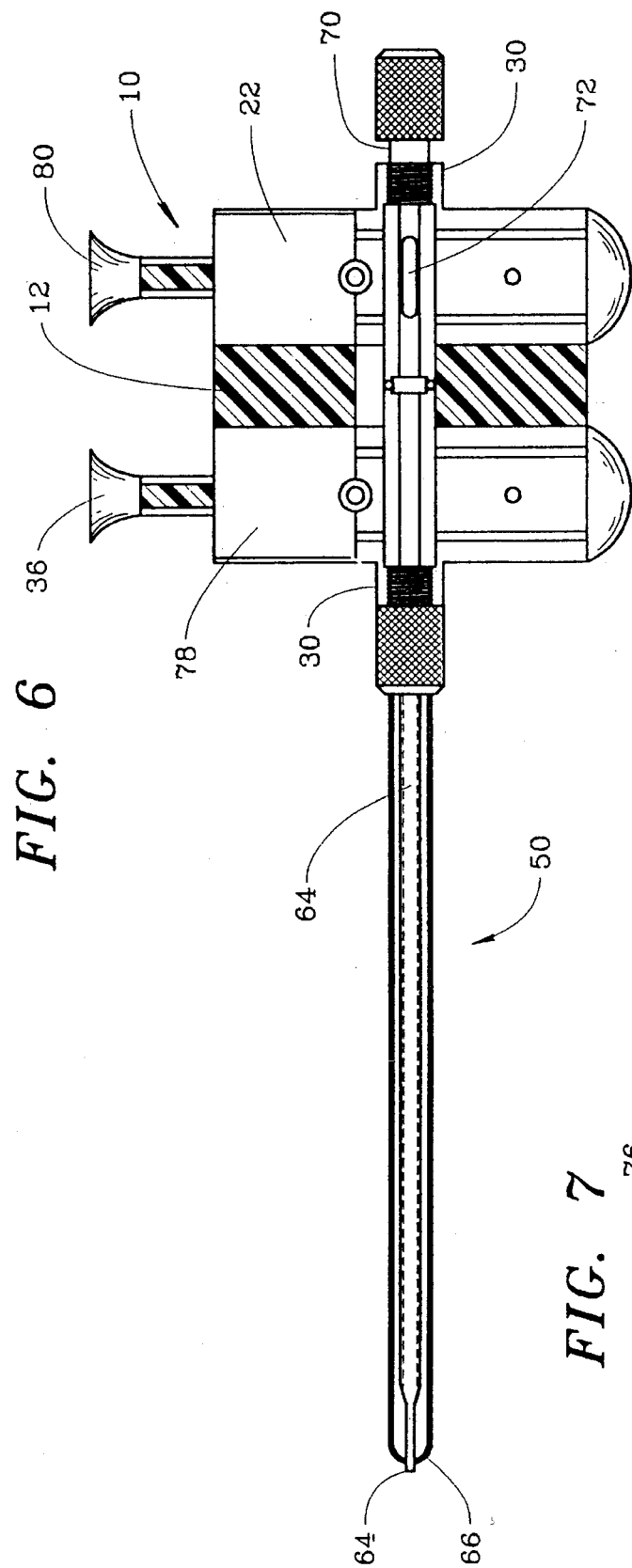
FIG. 6 is a cross sectional view of the symmetrical trumpet valve of FIG. 1 equipped with the first embodiment composite probe of the present invention.
Figure 7:
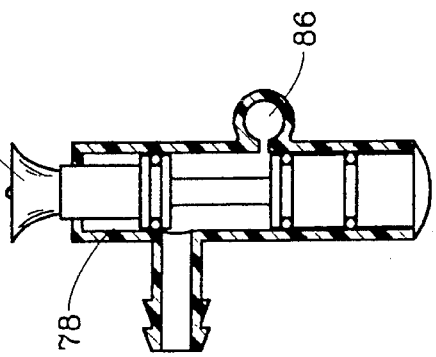
FIG. 7 is a perspective view of the first embodiment composite probe.

FIG. 6 illustrated, in cross section, a composite probe 50 of this invention installed on the trumpet valve of FIG. 1. In brief, each of the probe mounts 30 on the body of the irrigation valve are initially exposed. The outer or suction barrel 60 of the composite probe is installed first. The position of the suction barrel on the valve body is determined by clinician preference; more specifically, the preference of the clinician for right handed or left handed operation. Once the outer or suction barrel of the composite probe is installed, the inner or irrigation barrel 62 is thereafter put in place. Unlike the traditional mounting of a probe on the valve body, the orientation of the inner or irrigation barrel, relative to the valve body 12 is determined by the orientation of the outer or suction barrel. As illustrated in FIG. 6, the inner or irrigation barrel is mounted so as to pass through the valve body 12 and extend down the outer barrel 60 of the composite probe 50, with the tip 64 of the inner probe 62 extending through a port 64 in the distal end of the outer barrel designed to accommodate it. The inner probe is provided with a fitting 70 to seal the mount at the proximal end of the probe to the mount on the valve body. The side wall of the inner barrel is provided with a slot or opening 72 operatively connected to a pressurized source of irrigation fluid. In order to effectively isolate each of the valve chambers from one another and maintain separate and distinct functions for each of the outer barrel and inner barrel of the composite probe, an additional flexible seal, in the form of an "O" ring 74, is positioned and fixably mounted on the inner barrel approximately equidistant between each of the valve chambers so as to separate each of the chambers from one another. Thus, upon activation of either the suction or irrigation piston or the concurrent activation of both, each of the valve chambers are operatively connected to only one of the functional components of the composite probe. More specifically, upon simply the depression of the piston 76 associated with the suction chamber 78 as illustrated in FIG. 7, negative pressure is exerted at the distal end of the outer barrel of the composite probe, thereby effecting suction of fluid through the perforation in the distal end of the outer barrel, causing evacuation of fluid from the operative field. Similarly, where only the piston 80 associated with the irrigation valve chamber 82 is depressed, the pressurized fluid will flow from the chamber into the so-called "common channel" 86 and through the slot 72 in the side wall of the inner barrel 62, thus causing pressurized fluid to be directed onto the operative field through the distal end 64 of the irrigation probe.

Where both of the pistons 76, 80 associated with the suction 78 and irrigation 82 chambers are depressed so as to have both of the functions associated with each valve chamber operative at the same time, negative pressure will be exerted upon the distal end of the outer barrel concurrent with the flow of fluid through the distal end of the irrigation probe. The sealing 74 of the so-called "common channel" 86 between each of these chambers 78, 82 permits the concurrent operation of each of these pistons and the functional isolation of each of the respective valve chambers from one another.

Figure 8A:
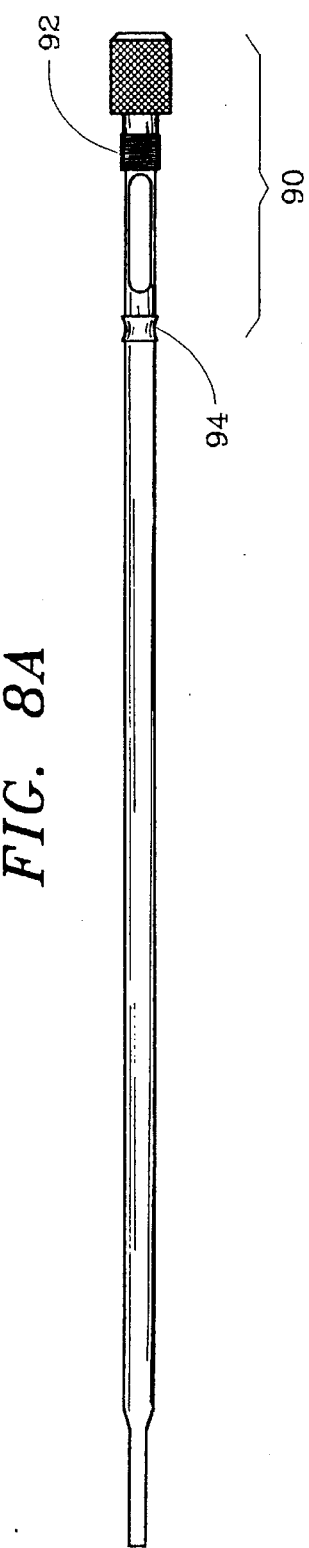
FIGS. 8a and 8b are a perspective view of the irrigation barrel of the first embodiment composite probe.
Figure 8B:
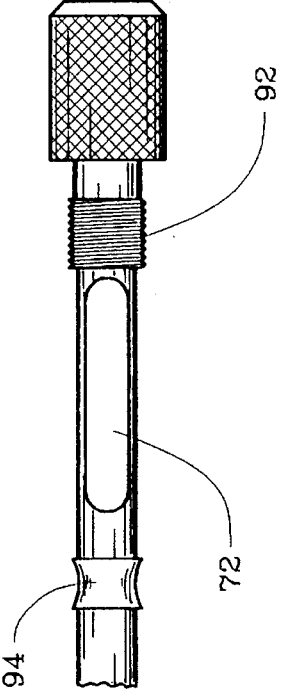
Figure 18:
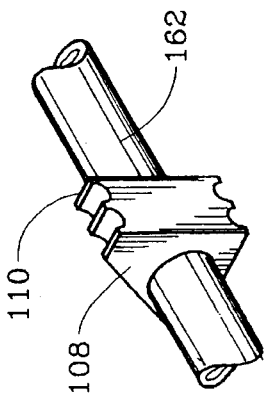
FIG. 18 is a perspective of a triangular shaped engagement nut attached to the inner cannula of the second embodiment of the present invention.

FIG. 8 illustrates in greater detail the inner barrel 62 of the composite probe. More specifically, the proximal end 90 of such probe is provided with means for attachment to the valve body in the form of a threaded fitting 92. As noted above, a slotted opening 72 is provided in the side wall to allow for infusion of fluid through the side wall into the common channel 86 of the irrigation probe. In the preferred embodiments of this invention, the slotted opening provides an orifice through the valve to allow for infusion of fluid from either side of the barrel. In the configuration of probe tip illustrated in FIG. 6, a raised collar 94 is machined into the probe tip to provide a means for support and retention of a flexible seal. The positioning of this raised collar is such as to effectively locate this seal between each of the chambers of the valve body so as to isolate one chamber from the other in the event either one or both pistons are depressed.

FIGS. 9–22 illustrates a second embodiment of the present invention wherein the inner cannula or barrel 162 and the outer cannula 162 are attached to the valve body 112 at the same probe mount end 130. This second embodiment utilizes the quick disconnect method of attaching/detaching probes from the valve body 112. The quick disconnect method and apparatus is the subject matter of my co-pending application Ser. No. 07/989,109, now abandoned filed on Dec. 11, 1992. The subject matter of Ser. No. 07/989,109 now abandoned is hereby incorporated by reference in its entirety into the instant application as if fully set forth herein.

As seen in FIGS. 9 and 10, the three components of the medical device and their relationship to one another reveals the basic valve body 112 having a threaded orifice for threading engagement with a complimentary thread of the first end of an adaptor 102. In the specific embodiment of this mating, adaptor 102 is removeably but securely engaged with valve body 112. The second end of adaptor 102 is provided for operative and rapid engagement and disengagement thereof with the composite probe 150. As the probe is easily and quickly removable from adaptor, numerous probes, having various probe tip configurations and diameters, can readily be interchanged, without replacing valve body 112 and adaptor 102, for various situations which can arise during surgery.

FIG. 9 shows a section of the valve body 112 showing adaptor 102 having threads and removeably connected to an interchangeable composite suction/irrigation probe 150 at probe mount base 161 of outer cannula 160. As adaptor 102 has threads at its first end it can be used with new or existing prior art valve bodies. As seen in FIG. 9, adaptor 102 is threaded on a first end (or distal portion thereof) which is removeably connected to valve body 112 and modified in a somewhat different fashion of a portion thereof which is designed for rapid coupling and de-coupling to an interchangeable composite probe 150 as well as numerous other probes (not shown). More specifically, adaptor 102 is further provided with a complimentary snap-lock seal, generally shown at 135, on the proximal end thereof including means for sealing engagement with probe 135 and means for snap lock engagement and disengagement at the proximal end of probe 150 with adaptor 102. Though adaptor 102 is shown removeably attached to the valve body 112, as described above, it is to be understood that adaptor 102 can be made integral with valve body 112 and still provide the snap/lock engagement with the composite probe 150.

Figure 17:
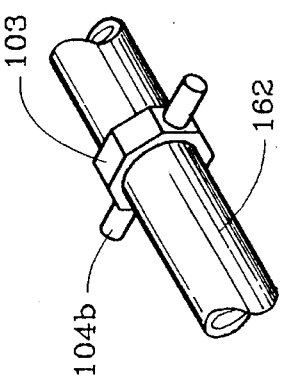
FIG. 17 is a perspective of the engagement nut of FIG. 13 welded to the inner cannula of the second embodiment of the present invention.
Figure 11:
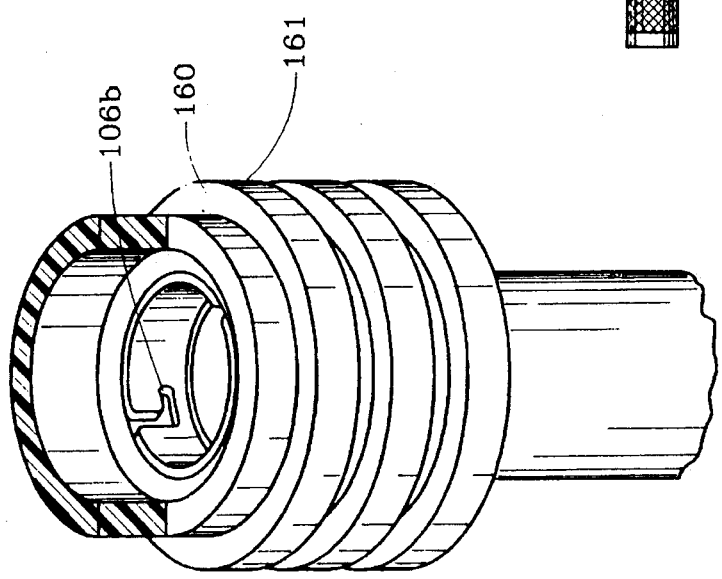
FIG. 11 is a partial sectional view of a portion of the outer cannula of the second embodiment of the present invention.
Figure 15:
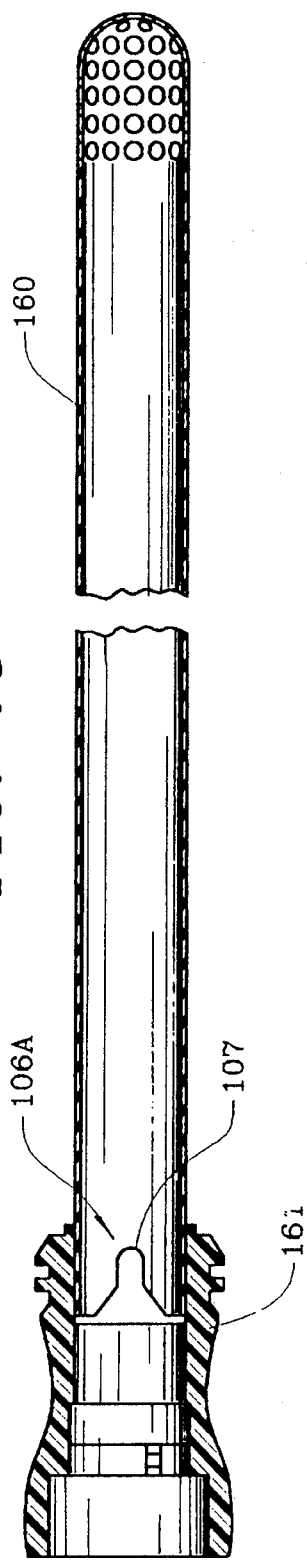
FIG. 15 is a sectional view of the outer cannula of the second embodiment of the present invention.
Figure 16:
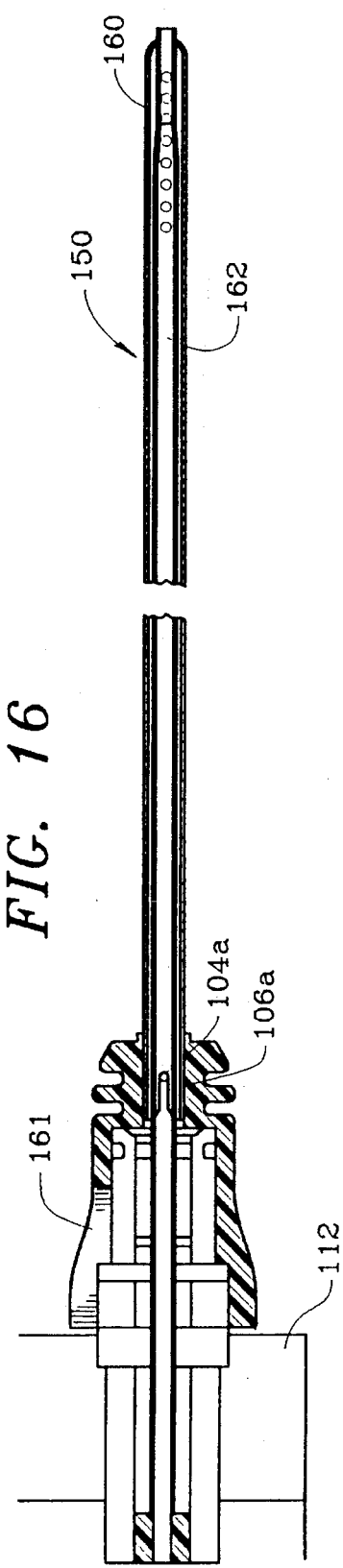
FIG. 16 is sectional view of the second embodiment of the present invention.
Figure 13:
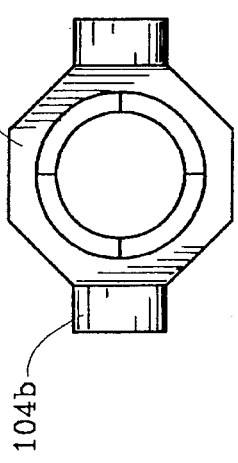
FIG. 13 is a front plan view of a engagement nut used in conjunction with the second embodiment of the present invention.
Figure 12:
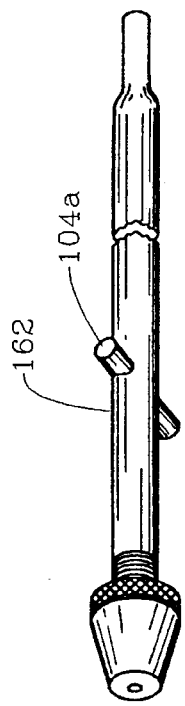
FIG. 12 is a perspective view of a portion of the inner cannula of the second embodiment of the present invention.
Figure 14:
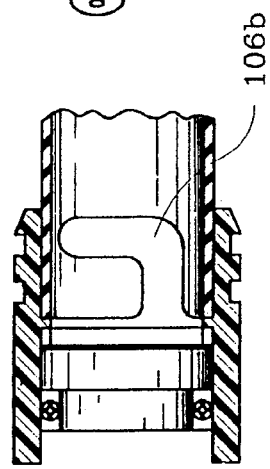
FIG. 14 is a sectional view of the outer cannula of FIG. 11.

The inner cannula or barrel 162 is removeably attached to the outer cannula or barrel 160. A pin 104a or 104b is provided on the inner barrel 162 for mating with a slot 106a or 106b disposed within the outer cannula 160. Pin 104 can either be inserted through the inner cannula 160 and protrude outward therefrom (FIG. 12) or the pin can be provided in conjunction with an engagement nut welded to the outer surface of the inner cannula 162 (FIGS. 13 and 17). Preferably, the slot 106a or 106b is disposed inside the base portion 161 of outer cannula 160. As illustrated in the figures, slot 106 can be substantially L-shaped (FIG. 11 and 14). In this design, once pin 104 is positioned in slot 106b, the outer cannula 160 or inner cannula 162 is rotated to lock the inner cannula 162 to the outer cannula 160 and thus providing and assuring proper orientation of inner cannula 162 with respect to outer cannula 160. FIGS. 15 and 16 illustrate an alternative shape for slot 106, which provides a snap-lock relationship between pin 104 and slot 106a A slight amount of pressure will allow pin 104 to be forced within the locking portion 107 of slot 106a. Once pin 104 is disposed within portion 107 of slot 106a, the inner cannula 162 is locked to the outer cannula 160 and thus guarantees the proper orientation between the respective cannulas 160 and 162. Though these two designs for the shape of the slot have been disclosed, the present invention is not limited to such designs and any shaped slot or pin configuration which will provide the locked relationship between the inner cannula 162 and outer cannula 160 is intended to be within the scope of the present invention. Though the pin 104 is protruding out from the inner cannula 162, sufficient room is still provided within the outer cannula 160 to allow blood, debris and other tissue fragments and the like to be suctioned through the outer cannula and to its dedicated port in common channel 186.

Figure 19:
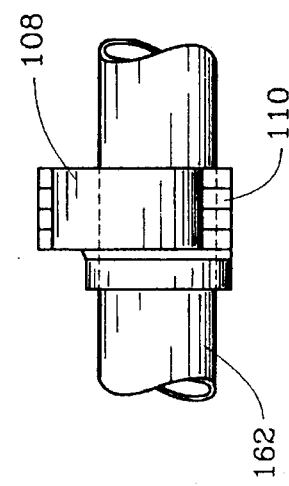
FIG. 19 is a front plan view of the triangular shaped engagement nut of FIG. 18.
Figure 20:
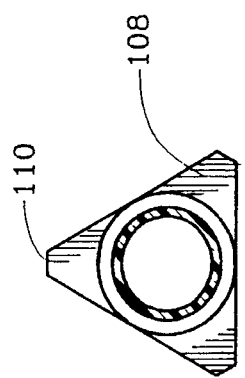
FIG. 20 is a partial front plan view showing the triangular shaped engagement nut of FIG. 18 attached to the inner cannula.
Figure 21:
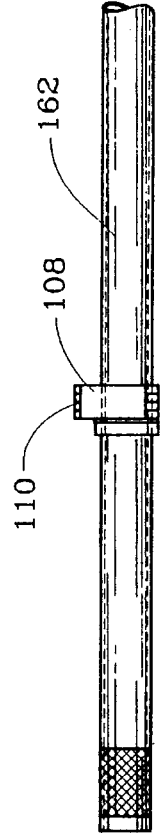
FIG. 21 is a front plan view showing the triangular shaped engagement nut of FIG. 18 attached to the inner cannula.

FIGS. 18–21 illustrate an alternative locking means for locking the inner cannula 162 to the outer cannula 160. As seen the pin/slot configuration is replaced by threads 110 and 111 located on the inner cannula 162 and outer cannula 160, respectively. Preferably, threads 111 are located within the probe base portion 161 of outer cannula 160. As seen a substantially triangular shaped piece 108 is attached, preferably by welding, to inner cannula 162. Piece 108 may be a threaded engagement nut as shown in FIG. 19. Threads 110 are provided on portions of piece 108 for mating with threads 111 located on the inner surface of the base portion 161 of outer cannula 160. Though piece 108 is shown as being substantially triangular it is to be understood that other shapes may be utilized as long as there is sufficient room within the outer cannula 160 for the flow therethrough of tissue and other debris. Once the inner cannula 162 has been locked to outer cannula 160 by their thread relationship, proper orientation is provided for the inner cannula 162 with respect to the outer cannula 160. The locked relationship between the cannulas, 160 and 162 provides for automatic alignment of the inner cannula 162 with respect to the outer cannula 160.

Once the inner cannula 162 is locked to outer cannula 160, the probe 150 is ready for mounting to the adaptor 102 of valve body 102 by the quick disconnect method mentioned above. This method replaces having to attached the cannulas 160 and 162 to separate probe mounts of valve body 112. As both cannulas 160 and 162 are locked together and attached to the same end of valve body 112 by the quick disconnect method, time is saved in switching and attaching various probes to the valve body 112.

A boss member 120 is provided on the inner cannula 162 for isolating the irrigation and suction ports 138 and 139, respectively, from each other. Boss member 120 is wedged into the narrow diameter portion of the hourglass shaped common channel 186 to separate the two chambers. However, it is to be understood that the boss member 120 can be utilized with the common channel 86 shape shown and described in the first embodiment of the present invention and still provide two discrete and dedicated ports. The boss member 120 replaces the O-ring seal 74 described above for creating independent ports. A cap or plug 165 is provided at the opposite probe mount end not used for attaching the composite probe 150 to the valve body 112.

Figure 22:
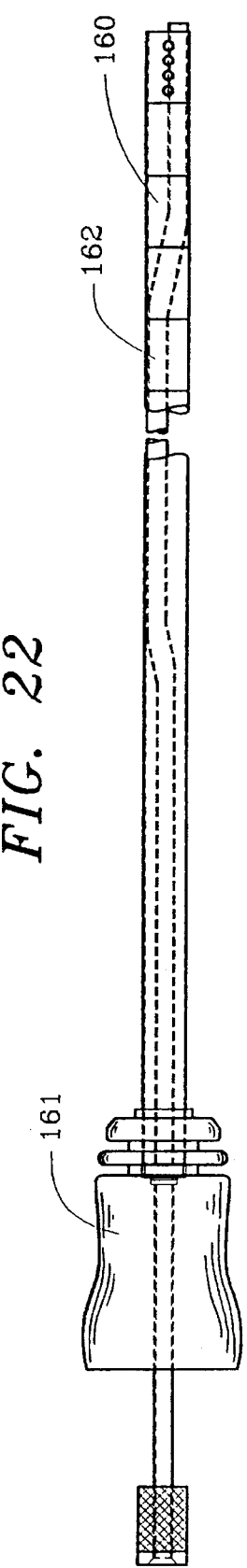
FIG. 22 is a front plan view of the second embodiment of the present invention illustrating an alternative design for the inner cannula.

FIG. 22 illustrates the inner cannula 162 having at least one bend in its design. The bending of the inner cannula 162 provides for stabilization of the inner cannula 162 within the outer cannula 160 and also provides a larger opening at the distal end of the composite probe 150 for suction purposes.

In use, the inner cannula 162 is attached to the outer cannula 160 by one of the locking methods described above. Once locked a first end 163 of the inner cannula 162 extends outward from the outer cannula 160 while a majority of the inner cannula 162 is disposed within the outer cannula 160. End 163 of inner cannula 162 is inserted within the common channel 186 and the outer cannula 162 is attached to the adaptor 102 by the quick disconnect method discussed above. This positioning of the cannulas 160 and 162 also causes the boss member 120 to be wedged within the narrow portion of the hourglass common channel 186 thus, effectively separating the two ports from each other. In this embodiment, opening 72 on the inner cannula 62 is not required as end 163 is open and positioned within the irrigation port when the cannulas 160 and 162 are attached to the valve body 112. Thus, irrigation flowing from the irrigation chamber of the valve flows into the isolated irrigation port 138 and into the inner cannula 162 at end 163 and out of the inner cannula at the opposite end 166. The operation and function of the valve and pistons are the same as the first embodiment of the present invention.

The instant invention has been shown and described herein in what is considered to be the most practical and preferred embodiments. It is recognized, however, that departures may be made therefrom within the scope of the invention and that obvious modifications will occur to a person skilled in the art.

What is claimed is:

1. A surgical valve in combination with a composite irrigation and suction probe, said composite probe releasably attached to said surgical valve for the delivery of a source of irrigation and suction, said surgical valve in combination with said probe comprising:

a single valve body having a common channel communicating with a plurality of valve chambers and at least one probe attachment end in fluid flow communication with the common channel, said valve body also including a plurality of valve means, each of said valve means operatively associated with a respective valve chamber, said common channel having an irrigation port and a suction port, said valve allowing for simultaneous suction and irrigation;

an inner cannula having a first end and a second end, said inner cannula having an internal passageway extending from said first end to said second end, the first end of said inner cannula disposed within the common channel between said suction port and said irrigation port of the common channel when said composite probe is removably attached to said surgical valve;

an outer cannula having a first end and a second end, said outer cannula having an internal passageway extending from said first end to said second end of said outer cannula, a portion of said inner cannula disposed within the internal passageway of said outer cannula;

means for properly orientating said inner cannula with respect to said outer cannula;

means for releasably attaching said outer cannula to said probe attachment end; and means for isolating said irrigation port and said suction port.

2. The combination valve and probe of claim 1 wherein said means for isolating is a boss member attached to the first end of said inner cannula and disposed within the common channel when said probe is attached to said valve to isolate and restrict fluid flow between said suction port and said irrigation port of the common channel.

3. The combination valve and probe of claim 1 wherein said means for properly orientating is a plurality of threads disposed on portions of a protruding member attached to said inner cannula and a plurality of threads disposed within an inner portion of said outer cannula, wherein when orientating said inner cannula with respect to said outer cannula the threads of said inner cannula and said outer cannula are mated together.

4. The combination valve and probe of claim 1 wherein said means for releasably attaching said outer cannula to the probe attachment end is an adaptor means for quick engagement and quick disengagement of an interchangeable probe member with said probe attachment end, said adaptor means having a first end and a second end, the first end of said adaptor means attached with the probe attachment end, the second end of said adaptor means removably attached with the first end of said outer cannula.

5. The combination valve and probe of claim 4 further including means for providing a sealed relationship between the first end of said outer cannula and the second end of said adaptor means.

6. The combination valve and probe of claim 5 wherein said means for providing a sealed relationship is an o-ring disposed around the second end of said adaptor means.

7. The combination valve and probe of claim 5 wherein said means for providing a sealed relationship is an o-ring disposed within an inner portion of said outer cannula near the first end of said outer cannula.

8. The combination valve and probe of claim 4 further including means for providing a snap/lock engagement and disengagement between the second end of said adaptor means and the first end of said outer cannula.

9. The combination valve and probe of claim 8 wherein said means for providing a snap/lock engagement and disengagement is a collar disposed around the second end of said adaptor means and a corresponding groove disposed within the first end of said outer cannula.

10. The combination valve and probe of claim 4 wherein said adaptor means is constructed integral with the valve body.

11. The combination valve and probe of claim 1 wherein said surgical valve is a trumpet valve.

12. The device of claim 1 wherein said inner cannula has at least one bend.

13. The combination valve and probe of claim 1 wherein said valve body comprising two valve chambers.

14. The combination valve and probe of claim 1 wherein said valve body comprising two probe attachment ends.

15. The combination valve and probe of claim 1 wherein said means for releasably attaching said outer cannula to the probe attachment end is an adaptor for quick engagement and quick disengagement of an interchangeable probe member with said probe attachment end, said adaptor means constructed integral with said valve body at said probe attachment end, said adaptor means removably attached with the first end of said outer cannula.

16. The combination valve and probe of claim 15 further including means for providing a sealed relationship between the first end of said outer cannula and said adaptor means.

17. The combination valve and probe of claim 16 wherein said means for providing a sealed relationship is an o-ring disposed around a portion of said interface means.

18. The combination valve and probe of claim 16 wherein said means for providing a sealed relationship is an o-ring disposed within an inner portion of said outer cannula near the first end of said outer cannula.

19. The combination valve and probe of claim 15 further including means for providing a snap/lock engagement and disengagement between said adaptor means and the first end of said outer cannula.

20. The combination valve and probe of claim 19 wherein said means for providing a snap/lock engagement and disengagement is a collar disposed around a portion of said adaptor means and a corresponding groove disposed within the first end of said outer cannula.

21. The combination valve and probe of claim 8 wherein said means for isolating is positioned at the first end of said inner cannula.

22. A surgical valve in combination with a composite irrigation and suction probe, said composite probe releasably attached to said surgical valve for the delivery of a source of irrigation and suction, said surgical valve in combination with said probe comprising:

a valve body having a common channel communicating with a plurality of valve chambers and at least one probe attachment end in fluid flow communication with the common channel, said valve body also including a plurality of valve means, each of said valve means operatively associated with a respective valve chamber, said common channel having an irrigation port and a suction port, said valve allowing for simultaneous suction and irrigation;

an inner cannula having a first end and a second end, said inner cannula having an internal passageway extending from said first end to said second end, the first end of said inner cannula disposed within the common channel between said suction port and said irrigation port of the common channel when said composite probe is removably attached to said surgical valve;

an outer cannula having a first end and a second end, said outer cannula having an internal passageway extending from said first end to said second end of said outer cannula, a portion of said inner cannula disposed within the internal passageway of said outer cannula;

means for properly orientating said inner cannula with respect to said outer cannula;

means for releasably attaching said outer cannula to said probe attachment end; and means for isolating said irrigation port and said suction port;

wherein said means for properly orientating is a plurality of threads disposed on portions of a protruding member attached to said inner cannula and a plurality of threads disposed within an inner portion of said outer cannula, wherein when orientating said inner cannula with respect to said outer cannula the threads of said inner cannula and said outer cannula are mated together;

wherein said protruding member is substantially triangular in shape.

23. A surgical valve in combination with a composite irrigation and suction probe, said composite probe releasably attached to said surgical valve for the delivery of a source of irrigation and suction, said surgical valve in combination with said probe comprising:

a valve body having a common channel communicating with a plurality of valve chambers and at least one probe attachment end in fluid flow communication with the common channel, said valve body also including a plurality of valve means, each of said valve means operatively associated with a respective valve chamber, said common channel having an irrigation port and a suction port, said valve allowing for simultaneous suction and irrigation;

an inner cannula having a first end and a second end, said inner cannula having an internal passageway extending from said first end to said second end, the first end of said inner cannula disposed within the common channel between said suction port and said irrigation port of the common channel when said composite probe is removably attached to said surgical valve.;

an outer cannula having a first end and a second end, said outer cannula having an internal passageway extending from said first end to said second end of said outer cannula, a portion of said inner cannula disposed within the internal passageway of said outer cannula;

means for properly orientating said inner cannula with respect to said outer cannula;

means for releasably attaching said outer cannula to said probe attachment end; and means for isolating said irrigation port and said suction port;

wherein said means for releasably attaching said inner cannula to said outer cannula is a pin member protruding outward from said inner cannula and a slot disposed within an inner surface of said outer cannula, wherein when attaching said inner cannula to said outer cannula said pin is removably secured within said slot.

24. A surgical valve in combination with a composite irrigation and suction probe, said composite probe releasably attached to said surgical valve for the delivery of a source of irrigation and suction, said surgical valve in combination with said probe comprising:

a valve body having a common channel communicating with a plurality of valve chambers and a plurality of probe attachment ends in fluid flow communication with the common channel, said valve body also including a plurality of valve means, each of said valve means operatively associated with a respective valve chamber, said common channel having an irrigation port and a suction port, said valve allowing for simultaneous suction and irrigation;

an inner cannula having a first end and a second end, said inner cannula having an internal passageway extending from said first end to said second end, the first end of said inner cannula disposed within the common channel between said suction port and said irrigation port of the common channel when said composite probe is removably attached to said surgical valve;

an outer cannula having a first end and a second end, said outer cannula having an internal passageway extending from said first end to said second end of said outer cannula, a portion of said inner cannula disposed within the internal passageway of said outer cannula;

means for properly orientating said inner cannula with respect to said outer cannula;

means for releasably attaching said outer cannula to said probe attachment end;

means for isolating said irrigation port and said suction port; and a cap means disposed within a second of the plurality of probe attachment ends.

25. A surgical valve in combination with a composite irrigation and suction probe, said composite probe releasably attached to said surgical valve for the delivery of a source of irrigation and suction, said surgical valve in combination with said probe comprising:

a valve body having a common channel communicating with a plurality of valve chambers and at least one probe attachment end in fluid flow communication with the common channel, said valve body also including a plurality of valve means, each of said valve means operatively associated with a respective valve chamber, said common channel having an irrigation port and a suction port, said valve allowing for simultaneous suction and irrigation;

an inner cannula having a first end and a second end, said inner cannula having an internal passageway extending from said first end to said second end, the first end of said inner cannula disposed within the common channel between said suction port and said irrigation port of the common channel when said composite probe is removably attached to said surgical valve;

an outer cannula having a first end and a second end, said outer cannula having an internal passageway extending from said first end to said second end of said outer cannula, a portion of said inner cannula disposed within the internal passageway of said outer cannula;

means for properly orientating said inner cannula with respect to said outer cannula;

means for releasably attaching said outer cannula to said probe attachment end; and means for isolating said irrigation port and said suction port;

wherein said common channel is shaped generally to resemble an hourglass with converging cylindrical channels to provide an interference fit and a sealed relationship between said common channel and said inner cannula end when said inner cannula is disposed within said common channel.

* * * * *

UNITED STATES PATENT AND TRADEMARK OFFICE
CERTIFICATE OF CORRECTION

PATENT NO. : 5,573,504
DATED : November 12, 1996
INVENTOR(S) : JAMES H. DORSEY III It is certified that error appears in the above-indentified patent and that said Letters Patent is hereby corrected as shown below:

Column 9, Line 54:  --with a base portion-- should be inserted after "first end".

Lines 59-63 should be deleted and the following should be substituted therefor:

--    probe attachment means on said base portion of said outer cannula for releasably attaching said outer cannula to said probe attachment end;

means for removably attaching and properly orienting said inner cannula with respect to said outer cannula; and--

Column 11, Line 12:  "8" should be --1--.

Signed and Sealed this

Fifteenth Day of April, 1997

Attest:

BRUCE LEHMAN

Attesting Officer     Commissioner of Patents and Trademarks